United States Patent [19]

Cho

[11] Patent Number: 4,752,426
[45] Date of Patent: Jun. 21, 1988

[54] PROCESS FOR MANUFACTURE OF PLASTIC RESINOUS TUBES

[75] Inventor: Tsuneo Cho, Hiroshima, Japan

[73] Assignees: Yoshito Ikada, Uji; Japan Medical Supply Co., Ltd., Hiroshima, both of Japan

[21] Appl. No.: 879,432

[22] Filed: Jun. 27, 1986

[30] Foreign Application Priority Data

Jun. 27, 1985 [JP] Japan ................ 60-141350
Dec. 2, 1985 [JP] Japan ................ 60-185904

[51] Int. Cl.[4] .................. B05D 3/06; B05D 7/22; B29C 71/04; C08J 7/18
[52] U.S. Cl. ........................ 264/22; 204/165; 204/168; 264/81; 264/83; 264/306; 264/347; 427/38; 427/45.1; 522/126; 522/134; 522/151; 522/153
[58] Field of Search ............... 264/22, 81, 83, 265, 264/306, 347; 204/165, 168; 427/38, 45.1; 522/126, 134, 151, 153

[56] References Cited

U.S. PATENT DOCUMENTS

| 3,600,122 | 8/1971 | Coleman | 204/165 X |
| 3,888,833 | 6/1975 | Lednicer et al. | 522/126 X |
| 4,131,691 | 12/1978 | Morley et al. | 204/165 X |
| 4,212,719 | 7/1980 | Osada et al. | 204/165 |
| 4,317,788 | 3/1982 | Imada et al. | 264/22 |
| 4,548,867 | 10/1985 | Ueno et al. | 264/22 X |

FOREIGN PATENT DOCUMENTS

| 120307 | 10/1984 | European Pat. Off. | 264/22 |
| 143082 | 7/1980 | Fed. Rep. of Germany | 264/22 |
| 49-51355 | 5/1974 | Japan | 264/22 |
| 50-19298 | 7/1975 | Japan | 264/22 |
| 55-29505 | 3/1980 | Japan . | |
| 56-147831 | 11/1981 | Japan | 264/22 |
| 59-98141 | 6/1984 | Japan | 264/22 |
| 60-110970 | 6/1985 | Japan | 264/22 |
| 61-89236 | 5/1986 | Japan | 427/38 |
| 2053026 | 2/1981 | United Kingdom | 427/45.1 |

OTHER PUBLICATIONS

Yasuda, H. e al., "Preparation of Reverse Osmosis Membranes by Plasma Polymerization of Organic Compounds," Journal of Applied Polymer Science, vol. 17 (1973), pp. 201-222.

Primary Examiner—Jeffery Thurlow
Assistant Examiner—Leo B. Tentoni
Attorney, Agent, or Firm—Cushman, Darby & Cushman

[57] ABSTRACT

Plastic resinous tubes, particularly for medical use is improved in blood compatibility when brought into contact with blood, by applying a low-temperature plasma treatment to inner surfaces of the tubes, which plasma is produced through electrodeless electric discharges by the effect of microwave to make it possible to prevent the tube from being heated in such a treatment. The inner surfaces of the tubes thus activated may be further subjected to an inner surface graft copolymerization treatment to enhance blood compatibility.

2 Claims, 1 Drawing Sheet

PROCESS FOR MANUFACTURE OF PLASTIC RESINOUS TUBES

BACKGROUND OF THE INVENTION 1. (Field of the Invention)

The present invention relates to a process for improving inner surface properties of plastic resinous tubes by subjecting such inner surfaces to a low-temperature plasma treatment.

2. (Description of the Prior Art)

Prior to filing the present application, it has already been conducted to improve surface properties of plastic resins particularly in hydrophilic and adhesive properties thereof, and also conducted to prevent plasticizers from being eluted, by means of the low-temperature plasma treatment of the surfaces of such plastic resinous goods. Further, it has also been known to conduct polymerization reactions of radical-polymerizable monomers by bringing the same into contact with a plenty of radicals produced on the surfaces of plastic resinous goods which have been subjected to the low-temperature plasma treatment, so as to conduct graft copolymerization reactions on the surfaces of the plastic resinous goods.

It has been known that the process in which the surface graft copolymerization reaction is conducted through such a low-temperature plasma treatment is superior in efficiency and safety to other processes such as processes in which gamma rays, electron rays or ultraviolet rays are irradiated for conducting such reactions, and to a process in which the treatment is conducted with ozone.

In a conventional low-temperature plasma treatment of the inner surfaces of the plastic resinous tubes, the sample is interposed between positive and negative electrodes so that electric discharges are conducted to produce plasma in a space between those electrodes, whereby the inner surfaces of the tubes are treated. Consequently, it is hard to conduct such a treatment efficiently.

Namely, since in the conventional treatment the electric discharge is conducted in a condition in which the electrodes are disposed at opposite ends of the plastic resinous tube, the tube to be subjected to such a treatment are inevitably restricted in length by a distance between the electrodes, and also restricted in number per operation in such a treatment. Those are the disadvantages inherent in the conventional treatment.

Consequently, the conventional process employing the above-mentioned treatment are not suitable for a need for efficiently treating a plenty of such tubes.

In order to solve the above disadvantages, there is proposed a process described in Japanese Patent Laid-Open No. 55-29505 (1980), in which process the tubes are inserted into cylindrical electrodes while the interior of the tubes are kept under a depressurized condition, and low-temperature plasma is produced to make it possible that the tubes are subjected to the low-temperature plasma treatment in the inner surfaces while the tubes are continuously in transit. However, it is technically difficult to uniformly treat the inner surfaces of the tubes by the use of this process. In addition to this disadvantage, such a process is further disadvantageous in that it requires a large-size apparatus provided with a relatively complex mechanism for carrying out the process, while still more gravely disadvantageous in that, since the process requires the electrodes and the treated surfaces to be brought close each other as the other conventional processes do, a rise in tube temperature in process is to an extent which cannot be ignored, resulting in thermal deformations or a formation of concave/convex defects on the treated surfaces.

Since these deformations and defects lead to a grave consequences, for instance, the case where such tubes deter the blood from flowing normally and/or produce a thrombus therein, in case these tubes are employed as medical plastic resinous tubes such as artificial blood vessels. Consequently, the conventional process above is not suitable for producing precise plastic resinous tubes.

SUMMARY OF THE INVENTION

It is an object of the present invention to eliminate the above defects, and more particularly: first, to provide a process for conducting a low-temperature plasma treatment which enables the plastic resinous tubes not to be subjected to any deformation and concave/convex defects on the inner and outer surfaces at the time of processing the inner surfaces and also enables the tubes to be treated to have uniformly finished inner surfaces; second, to provide a process for conducting graft copolymerization of the inner surfaces of the tubes by the use of the low-temperature plasma treatment; third, to provide a process for conducting the low-temperature plasma treatment of the inner surfaces of the plastic resinous tubes efficiently.

These objects of the present invention are accomplished by: essentially, generating a low-temperature plasma gas through electrodeless electric discharges by means of microwave so that the plasma gas thus generated is introduced from a plasma generating station into a plastic resinous tubes disposed at a position spaced apart from the plasma generating station so as to be brought into contact with inner surfaces of the plastic resinous tubes; and additionally, bringing the inner surfaces of the tubes having been subjected to the low-temperature plasma treatment into contact with radical-polymerizable monomers to conduct an inner surface graft copolymerization reaction.

In an electrodeless electric discharge process by means of irradiation of microwave according to the present invention, there is not any electrode within an electric discharge space (area). Yet the plasma generated by this process is remarkably high in volume and density compared to other processes. This process according to the present invention can take out continuously a gas which contains enough volume of low-temperature plasma out of the electric discharge space, because this process can conduct an electric discharge process of a depressurized gas which is introduced into the space continuously.

The plasma thus obtained is then introduced into the plastic resinous tubes so as to be brought into contact with the inner surfaces of the tubes, to make it possible that the inner surfaces of the tubes are treated in a position spaced apart from the electric discharge station. Consequently, the treated items (tubes) are not subjected to direct influence of the microwave and the electric discharge. This is one of advantages of the process of the present invention.

Therefore, according to the present invention, in case the treated items are adequately spaced away from the electric discharge station, there is no fear that the treated items are extraordinarily heated to cause deformation or deterioration in quality, or no fear that the treated items are subjected to concave/convex defects on the inner and outer surfaces of the same under the influence of the electric discharge.

Further, according to the present invention, in case the radical-polymerizable monomers in the form of gas or liquid are introduced into the plastic resinous tubes so as to be brought into contact with the inner surfaces of the tubes, a polymerization reaction occurs to produce graft copolymers on the inner surfaces of the tubes resulting in improvement of the property of the inner surfaces.

DESCRIPTION OF THE PREFERRED EMBODIMENTS

Figure 1:
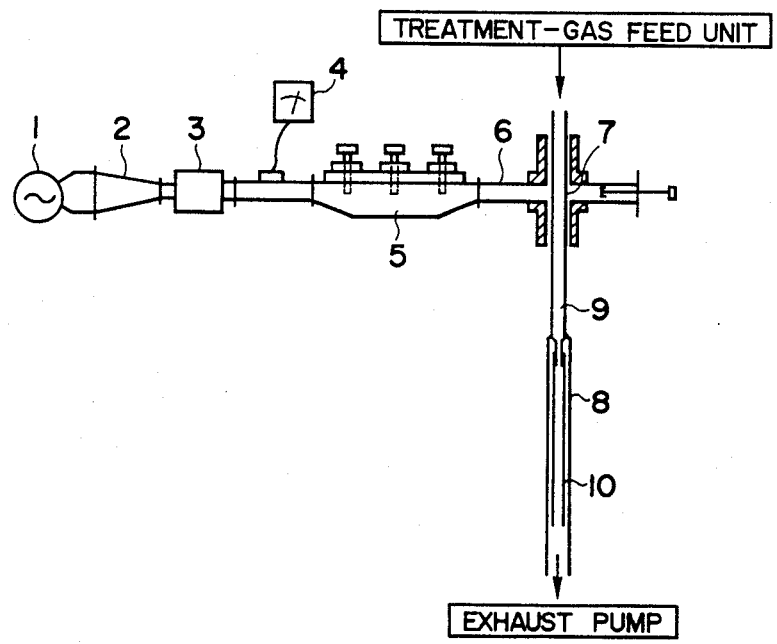
FIG. 1 is a schematic view of a basic construction of an embodiment of a low-temperature plasma treatment apparatus for carrying out the process of the present invention.

Now, the process of the present invention will be hereinbelow described with reference to the drawings. FIG. 1 shows a basic construction of a microwave plasma treatment apparatus for carrying out the process of the present invention, which apparatus comprises: an oscillator 1: a tapered waveguide 2; an isolator 3; a power monitor 4; a stubbed tuner 5; a plasma applicator 6; a plasma chamber 7; a treating chamber 8; a conduit 9; and an exhaust pump for depressurizing the plasma chamber 7 and treating chamber 8. A 2450 mega herz micorwave serves as an energy source of this apparatus.

The isolator 3 is provided for the purpose of stabilizing the operation of the oscillator 1 even under a condition in which the plasma applicator, which is to absorb the microwave, is subjected to no load. The power monitor 4 is provided in the apparatus for monitoring a reflected microwave.

How this apparatus works will be described as follows: The microwave generated in the oscillator 1 is ultimately transferred to the plasma applicator 6 where the microwave is absorbed by a gas in the plasma chamber 7 made of quartz disposed at a position where a maximum electric field of the microwave exists in the plasma applicator 6, so that the gas in the plasma chamber 7 may be activated into a plasma state. The plasma gas thus activated is introduced into the treating chamber 8 through the conduit 9. As shown in FIG. 1, since the plastic tube 10 to be treated is attached to a foremost end of the conduit 9, the plasma gas thus introduced is brought into contact with the inner surfaces of the tube 10 to activate the inner surfaces of the same 10. A treating chamber 8 receives the plastic resinous tube 10 for plasma treatment of the same 10 and works as a means for preventing the tube from collapsing under the influence of the outer atmospheric pressure. Incidentally, it is preferable that the pressure in both the treating chamber 8 and the tube 10 is within a range of from about 0.01 to 10 mm Hg.

Figure 2:
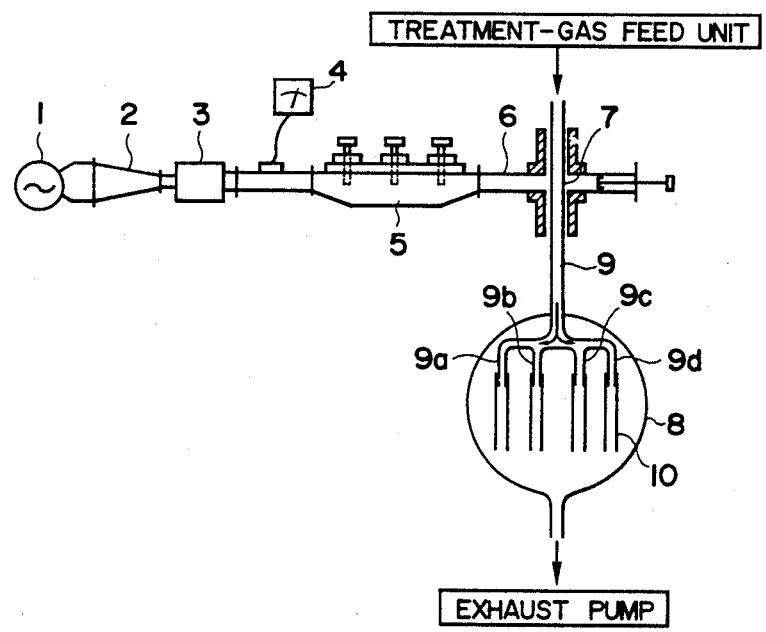
FIG. 2 is a schematic view of a basic construction of another embodiment of the low-temperature plasma treatment apparatus for carrying out the process of the present invention.

The apparatus shown in FIG. 1 treats one tube at one time. In order to treat a plurality of the tubes at once, the end portion of the conduit 9 may be branched off into branch conduits 9a, 9b, 9c and 9d so as to take a manifold-like shape as shown in FIG. 2. In this case, it is preferable that each of the mounting positions of the tubes is equally spaced apart from the branching point of the conduit 9.

Next, the process where the graft copolymerization reaction is conducted on the inner surfaces of the tube will be explained. The inner surfaces of the tube 10 subjected to the plasma treatment already described are brought into contact with a solution or a vapor of radical-polymerizable monomers. In this case, though such an operation may be conducted at a room temperature, appropriate heating or cooling is applicable to such an operation to control the progress of the operation.

The radical-polymerizable monomers to be used are acrylamide, dimethyl acrylamide, methacrylamide, vinylpyrrolidone, acrylic acid, methacrylic acid, esters of acrylic acid or esters of methacrylic acid, vinyl acetate, styrene and vinyl chloride. Among the above, monomers polymerizable into water-soluble polymers, when polymerized homogeneously, are preferable.

EXAMPLE 1

In the apparatus (microwave output: 1 kW) as shown in FIG. 1, the inner surfaces of polyurethane tubes and tubes made of ethylene-vinyl acetate copolymer (EVA), each tube being 3 mm in inner diameter and 30 cm in length are subjected to a low-temperature plasma treatment. Oxygen gas serves as a treatment gas under a pressure of 0.07 mm Hg so that the low-temperature plasma treatment is conducted for 10 seconds and 60 seconds, respectively.

Then the tubes thus subjected to a low temperature plasma treatment are immersed in a 10% acrylamide solution to conduct polymerization at a temperature of 60° C. for six hours, and after that, washed with hot water to remove residual unpolymerized monomers and homopolymers produced during this polymerization reaction.

Graft polymerization amount in each inner surface of opposite end portions and a central portion of the tubes thus obtained is measured to evaluate the uniformity of the treatment. The result is shown in Table 1. Incidentally, the measurement of the graft polymerization amount is conducted as follows:

First, each portion of the tubes to be measured is cut into pieces to be immersed in a 1.5N hydrochloric acid (HCl) solution and then polyacrylamide is hydrolyzed in an autoclave under a pressure of 1.5 atmospheric pressure for 30 minutes. The tubes are then neutralized with sodium hydroxide (NaOH), and after that a ninhydrin solution is added. Then the tubes are treated again in the autoclave under 1.5 atmospheric pressure for five minutes to measure the absorbance of the obtained reaction solution in a light wavelength of 570 nm. The measured values thus obtained are employed to calculate the graft polymerization amount in comparison with a previously prepared calibration chart.

TABLE 1

| No. | Materials of Tubes | Plasma Treatment Time (sec) | Graft Polymerization Amount ($\mu g/cm^2$) | | |
|---|---|---|---|---|---|
| | | | Left End Portion | Central Portion | Right End Portion |
| 1 | Polyurethane | 10 | 8.3 | 12 | 12 |
| 2 | Polyurethane | 10 | 9.1 | 7.5 | 11 |
| 3 | Polyurethane | 60 | 16 | 19 | 18 |
| 4 | EVA | 60 | 11 | 11 | 13 |

REFERENCE SAMPLE 1

Polyurethane tubes having an inner diameter of 3 mm and a length of 30 cm are subjected to a low-temperature plasma treatment under a pressure of 0.8 mm Hg for 5 seconds and 30 seconds respectively by the use of a glow discharge unit provided with needle-like electrodes.

The tubes thus treated are graft-polymerized with acrylamide as in the Example 1, and then polymerization amount is measured. The result is shown in Table 2 as follows:

TABLE 2

| No. | Materials of Tubes | Plasma Treatment Time (sec) | Graft Polymerization Amount ($\mu g/cm^2$) | | |
|---|---|---|---|---|---|
| | | | Left End Portion | Central Portion | Right End Portion |
| 5 | Polyurethane | 5 | 4.8 | 1.6 | 3.3 |
| 6 | Polyurethane | 30 | 3.6 | 0.0 | 15 |

REFERENCE SAMPLE 2

EVA tubes having an inner diameter of 3 mm and a length of 30 cm are subjected to a low-temperature plasma treatment under a pressure of 0.2 mm Hg for 10 seconds by the use of a high-frequency discharge unit having an output of 50 W and a frequency of 13.56 mega herz.

The tubes thus treated are graft-polymerized with acrylamide as in Example 1, and then polymerization amount is measured. The result is shown in Table 3 as follows:

TABLE 3

| No. | Materials of Tubes | Plasma Treatment Time (sec) | Graft Polymerization Amount ($\mu g/cm^2$) | | |
|---|---|---|---|---|---|
| | | | Left End Portion | Central Portion | Right End Portion |
| 7 | EVA | 10 | 10 | 1.1 | 4.2 |
| 8 | EVA | 10 | 12 | 17 | 0.0 |

EXAMPLE 2

A polyurethane tube having an inner diameter of 3 mm and a length of 120 cm is subjected to a low-temperature plasma treatment for 60 seconds as in Example 1, and after that further subjected to a graft polymerization treatment. The graft polymerization amounts at both of the ends and three positions of four equally sectioned tube are 7.3, 4.5, 4.2, 6.9, and 5.3 $\mu g/cm^2$, respectively.

As it is clear from the above results, by means of the process according to the present invention, the entire inner surfaces of the tube can be uniformly subjected to a low-temperature plasma treatment.

As stated before, the plastic resinous tubes according to the present invention are not subjected to the direct influence of electric discharges. Therefore it is possible to obtain tubes with the inner surfaces having a smooth finish. There is no fear that the tubes are subjected to thermal deformation to deterioration in quality and/or to concave/convex defects in the inner and outer surfaces of the tubes. As a result, the tubes can be processed so that the tubes may have smooth outer and inner surfaces.

Further, the process of the present invention enables long tubes to be speedily and uniformly treated, to make it possible to efficiently produce the products with a stable quality.

Therefore, in case the present invention is applied to manufacture of medical plastic resinous tubes, it is possible to obtain a remarkably favorable effect, since the tubes manufactured according to the present invention are superior in blood compatibility to conventional tubes manufactured through other plasma treatments, when brought into contact with blood on their inner surfaces. Especially, in case blood compatibility is improved by means of graft-copolymerization on the inner surfaces of the tubes, this remarkably favorable effect can further be increased by a combination of both of the treatments.

Consequently, the present invention is particularly applicable to manufacture of medical plastic resinous tubes which contact blood, for example, artificial blood vessels and catheters and blood circulation units.

What is claimed is:

1. A process for manufacture of bio-compatible plastic resinous tubes for medical use, comprising the steps of:
   producing low-temperature plasma in a plasma chamber through electrodeless electric discharges caused by microwave;
   introducing the plasma thus generated into plastic resinous tubes disposed in a position spaced apart from the plasma chamber to activate the inner surfaces of said plastic resinous tubes; and
   introducing radical-polymerizable monomers into said plastic resinous tubes to graft-polymerize said monomers into polymers in the inner surfaces of said plastic resinous tubes having been activated by said plasma.

2. The process for manufacture of bio-compatible plastic resinous tubes as set forth in claim 1, wherein:
   said radical-polymerizable monomers are monomers which are polymerized into water-soluble monomers when polymerized homogeneously; and
   said radical-polymerizable monomers being one or more compound selected from the group consisting of acrylamide, dimethyl acrylamide, methacrylamide and vinylpyrrolidone.

* * * * *